(12) United States Patent
Daly et al.

(10) Patent No.: US 11,707,569 B2
(45) Date of Patent: Jul. 25, 2023

(54) FRONT-LOADABLE FLUID TRANSFER ASSEMBLIES AND RELATED MEDICAL FLUID TRANSFER SYSTEMS AND METHODS

(71) Applicant: ClearPoint Neuro, Inc., Irvine, CA (US)

(72) Inventors: Maxwell Jerad Daly, Redlands, CA (US); Peter G. Piferi, Orange, CA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 331 days.

(21) Appl. No.: 17/032,140

(22) Filed: Sep. 25, 2020

(65) Prior Publication Data

US 2021/0187188 A1    Jun. 24, 2021

Related U.S. Application Data

(60) Provisional application No. 63/076,008, filed on Sep. 9, 2020, provisional application No. 62/950,521, filed on Dec. 19, 2019.

(51) Int. Cl.
| | |
|---|---|
| *A61M 5/145* | (2006.01) |
| *A61K 35/28* | (2015.01) |
| *A61M 5/315* | (2006.01) |
| *A61M 25/01* | (2006.01) |
| *A61M 39/10* | (2006.01) |
| *A61M 5/14* | (2006.01) |

(52) U.S. Cl.
CPC ........... *A61M 5/1452* (2013.01); *A61K 35/28* (2013.01); *A61M 5/31513* (2013.01); *A61M 5/31528* (2013.01); *A61M 25/0102* (2013.01); *A61M 39/10* (2013.01); *A61M 2005/1403* (2013.01); *A61M 2025/0166* (2013.01); *A61M 2202/09* (2013.01); *A61M 2205/0266* (2013.01); *A61M 2210/0693* (2013.01)

(58) Field of Classification Search
CPC ............... A61B 17/3478; A61K 35/28; A61M 2005/1403; A61M 25/0102; A61M 5/1452; A61M 5/31528
See application file for complete search history.

(56) References Cited

U.S. PATENT DOCUMENTS

| | | | | |
|---|---|---|---|---|
| 4,955,863 | A | * | 9/1990 | Walker .............. A61M 25/0014 604/165.02 |
| 5,699,801 | A | | 12/1997 | Atalar et al. |
| 5,928,145 | A | | 7/1999 | Ocali et al. |

(Continued)

FOREIGN PATENT DOCUMENTS

EP          2558154 A2      2/2013

OTHER PUBLICATIONS

International Search Report and the Written Opinion of the International Searching Authority corresponding to International Patent Application No. PCT/US2020/052707 (15 pages) (dated Dec. 11, 2020).

*Primary Examiner* — Deanna K Hall
(74) *Attorney, Agent, or Firm* — Myers Bigel, P.A.

(57) ABSTRACT

Devices for transferring fluid to or from a subject include a plunger assembly coupled to or coupleable to a cannula assembly to allow target fluid to be "front-loaded" into a distal end of the cannula assembly while the stylet is withdrawn a distance to create a vacuum and define a flow channel.

17 Claims, 10 Drawing Sheets

(56) References Cited

U.S. PATENT DOCUMENTS

| | | |
|---|---|---|
| 6,050,992 A | 4/2000 | Nichols |
| 6,167,311 A | 12/2000 | Rezai |
| 6,263,229 B1 | 7/2001 | Atalar et al. |
| 6,284,971 B1 | 9/2001 | Atalar et al. |
| 6,356,786 B1 | 3/2002 | Rezai et al. |
| 6,405,079 B1 | 6/2002 | Ansarinia |
| 6,438,423 B1 | 8/2002 | Rezai |
| 6,526,318 B1 | 2/2003 | Ansarinia |
| 6,539,263 B1 | 3/2003 | Schiff et al. |
| 6,606,513 B2 | 8/2003 | Lardo |
| 6,609,030 B1 | 8/2003 | Rezai et al. |
| 6,628,980 B2 | 9/2003 | Atalar et al. |
| 6,675,033 B1 | 1/2004 | Lardo et al. |
| 6,701,176 B1 | 3/2004 | Halperin et al. |
| 6,708,064 B2 | 3/2004 | Rezai |
| 6,904,307 B2 | 6/2005 | Karmarkar et al. |
| 8,175,677 B2 | 5/2012 | Sayler et al. |
| 8,315,689 B2 | 11/2012 | Jenkins et al. |
| 8,374,677 B2 | 2/2013 | Piferi et al. |
| 9,891,296 B2 | 2/2018 | Piferi |
| 2003/0028095 A1 | 2/2003 | Tulley |
| 2003/0050557 A1 | 3/2003 | Susil et al. |
| 2004/0046557 A1 | 3/2004 | Karmarkar et al. |
| 2010/0198052 A1 | 8/2010 | Jenkins et al. |
| 2017/0151416 A1 | 6/2017 | Kutikov et al. |
| 2017/0232229 A1* | 8/2017 | Flores ............... A61M 25/0097 604/506 |
| 2019/0346516 A1 | 11/2019 | Piferi |

* cited by examiner

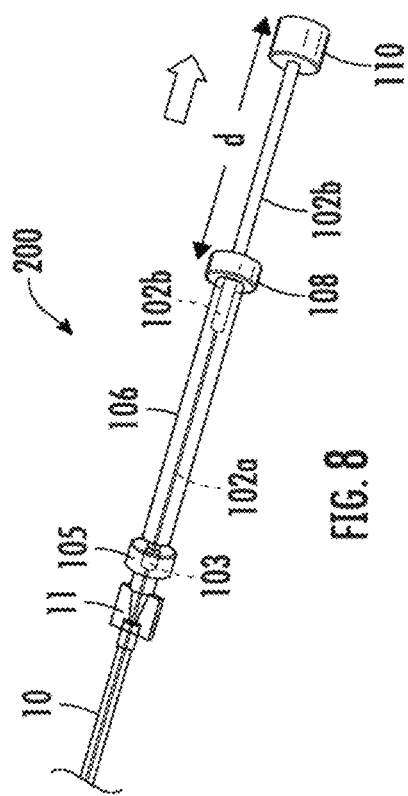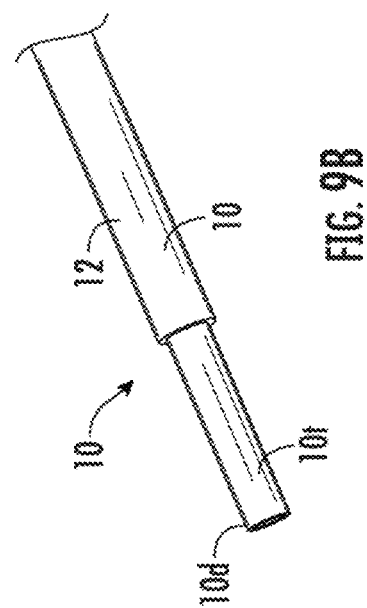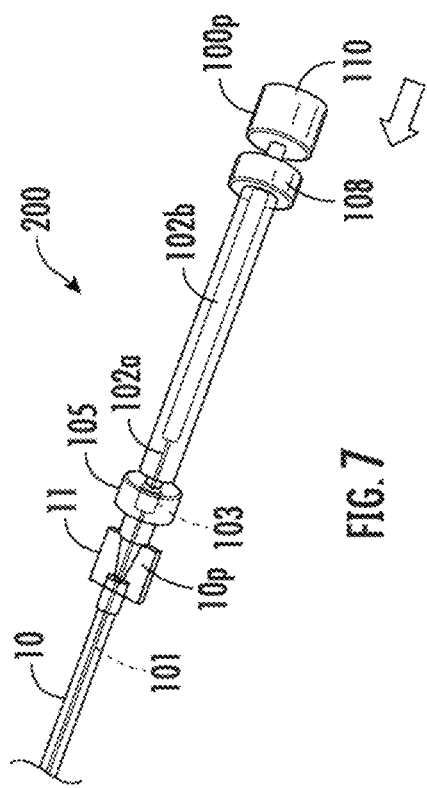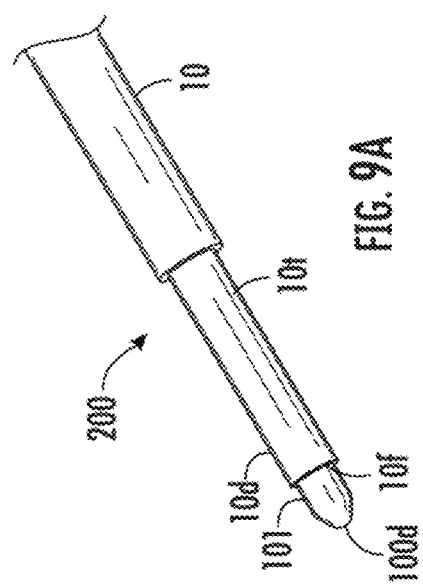

FRONT-LOADABLE FLUID TRANSFER ASSEMBLIES AND RELATED MEDICAL FLUID TRANSFER SYSTEMS AND METHODS

RELATED APPLICATIONS

This application claims the benefit of and priority to U.S. Provisional Patent Application Ser. No. 62/950,521 filed Dec. 19, 2019, and U.S. Provisional Patent Application Ser. No. 63/076,008 filed Sep. 9, 2020, the contents of which are hereby incorporated by reference as if recited in full herein.

FIELD OF THE INVENTION

The present invention relates generally to medical devices and systems and, more particularly, to devices and systems for delivering and/or withdrawing substances in vivo.

BACKGROUND

Various therapeutic and diagnostic procedures require that a substance be delivered (e.g., infused) into or aspirated from a prescribed region of a patient, such as to an intrabody target using a delivery device. It may be important or critical that the substance be delivered or removed with accuracy to the target region in the patient and without undue trauma to the patient.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the invention are directed to front-loadable fluid transfer assemblies for transferring fluid to or from a subject.

Embodiments of the invention are directed to a surgical plunger assembly that includes: a stylet comprising opposing proximal and distal ends; a luer connector comprising an internal seal coupled to the stylet; and a support body coupled to the luer connector and extending above the distal end of the stylet. The support body encloses a sub-length of the stylet and the stylet is longitudinally moveable relative to the support body between first and second positions. In the first position, the proximal end of the stylet is closer to the luer connector than in the second position.

The plunger assembly can also include a plunger comprising a first segment coupled to or defined by the stylet and a second segment having a greater cross-sectional size that the first segment. The second segment can merge into an external plunger flange. The support body can enclose the first segment and at least a portion of the second segment and the first segment and the second segment can be longitudinally movable relative to the support body. With the plunger in a first position, the stylet is in the first position and the second segment of the stylet resides closer to the luer connector than when the stylet is in the second position.

The plunger assembly can further include a drive screw that resides at least partially in the support body and that is coupled to the proximal end of the stylet.

The plunger assembly can further include a collar that is coupled to the support body and the drive screw. The collar can be rotatable in clockwise and counterclockwise directions to translate the stylet.

The plunger assembly can further include a support tube residing inside the support body and coupled to the luer connector above the seal. The stylet can be slidably coupled to the support tube to retract and extend inside the support tube while the support body slidably retracts and extends in concert with the stylet about an outer wall of the support tube.

Embodiments of the invention are directed to a surgical plunger assembly that includes: a stylet having opposing proximal and distal ends; a luer connector having an internal seal residing adjacent the proximal end of the stylet; a support body coupled to the luer connector and extending above the distal end of the stylet; and a plunger with a first segment coupled to or defined by the stylet and a second segment having a greater cross-sectional size that the first segment. The second segment merges into an external plunger flange. The support body encloses the first segment and at least a portion of the second segment and the first segment and the second segment are longitudinally movable relative to the support body. With the plunger in a first position, the second segment resides closer to the luer connector than in a second position.

The stylet can have a length outside the support body that is in a range of 6 inches and 10 feet in one or both of the first and second positions.

The stylet can have a length outside the support body that is in a range of 6 inches and 10 feet when the plunger is in each of the first and second positions.

The stylet can be formed of an MM compatible material and can have a maximal outer diameter in a range of about 0.005 inches and about 0.020 inches.

The stylet can be formed of Nitinol.

The stylet can be formed of fused silica.

Other embodiments are directed to an intrabody fluid transfer system that includes: a cannula assembly with a proximal end with a luer connector and having a longitudinally opposing distal end with an open channel extending therethrough; and a plunger assembly coupled to the cannula assembly. The plunger assembly can have a stylet that extends in the open channel of the cannula assembly to position a distal end of the stylet adjacent the distal end of the cannula assembly. The open channel and the stylet cooperate to define a fluid channel extending from the distal end of the cannula assembly, optionally having a length in a range of about 1 cm to about 30 cm.

With the plunger in a first position associated with a ready to intake fluid or a fully injected position, the distal end of the stylet can extend flush with or out of the distal end of the cannula assembly.

Fluid can be held for dispensing to a patient in the fluid channel at a location between the distal end of the cannula assembly and a medial portion of the cannula assembly.

The plunger assembly can further include a luer connector with an internal seal residing adjacent the stylet. The luer connector of the plunger assembly can be attached to the luer connector of the cannula assembly. The plunger assembly can also include a support body coupled to the luer connector of the plunger assembly and extending above the distal end of the stylet and a plunger having a first segment coupled to or defined by the stylet and a second segment having a greater cross-sectional size that the first segment. The second segment can merge into an external plunger flange. The support body can enclose the first segment and at least a portion of the second segment and the first segment and the second segment can be longitudinally movable relative to the support body. With the plunger in a first position, the second segment can reside closer to the luer connectors than in a second position.

The intrabody fluid transfer assembly can further include a drive screw that resides at least partially in the support body and that is coupled to the proximal end of the stylet.

The intrabody fluid transfer assembly can further include a collar that is coupled to the support body and the drive screw. The collar can be rotatable in clockwise and counterclockwise directions to translate the stylet.

The intrabody fluid transfer assembly can further include a support tube residing inside the support body and coupled to the luer connector above the seal. The stylet can be slidably coupled to the support tube to retract and extend inside the support tube while the support body slidably retracts and extends in concert with the stylet about an outer wall of the support tube.

The stylet can have a length outside the support body that is in a range of 6 inches and 10 feet when the plunger is in each of the first and second positions.

The stylet can be formed of an MRI compatible material and can have a maximal outer diameter in a range of about 0.005 inches and about 0.020 inches.

The stylet can be formed of Nitinol.

The stylet can be formed of fused silica.

Other embodiments are directed to methods for transferring fluid into or from a subject. The methods include: providing a cannula assembly having a luer connector on a proximal end thereof and having a longitudinally opposing distal end; and providing a plunger assembly that is coupleable to or coupled to the cannula assembly. The plunger assembly has a stylet extending from the proximal end to a position proximate, flush with or beyond the distal end of the cannula assembly. The methods further include creating a vacuum by withdrawing the stylet relative to the distal end of the cannula assembly; and intaking target fluid into the distal end of the cannula assembly in response to the vacuum created by the stylet and the cannula assembly.

The methods can also include placing the cannula assembly with the plunger assembly coupled thereto and holding the fluid into a trajectory guide of a surgical navigation system whereby a proximal end portion of the plunger assembly is above the trajectory guide and the distal end of the cannula assembly and stylet are in a body of a patient and transferring the fluid into the patient.

The fluid can include stem cells.

The method can further include delivering the fluid to an intrabrain target site for the transferring step.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 7 is a side perspective view of a proximal end portion of the assembled device shown in FIG. 3 with the plunger in position for actuation for intaking fluid at the distal end thereof according to embodiments of the present invention.

FIG. 8 is a side perspective view of the proximal end portion of the assembled device shown in FIG. 7 with the plunger in a second position for actuation for dispensing/injecting fluid at the distal end thereof according to embodiments of the present invention.

FIG. 9A is an enlarged distal end perspective view of the assembled device shown when in the position of FIG. 7.

FIG. 9B is an enlarged distal end perspective view of the assembled device shown when in the position of FIG. 8.

FIG. 15 is a flow chart of exemplary actions that can be carried out according to embodiments of the present invention.

DETAILED DESCRIPTION

Figure 1:
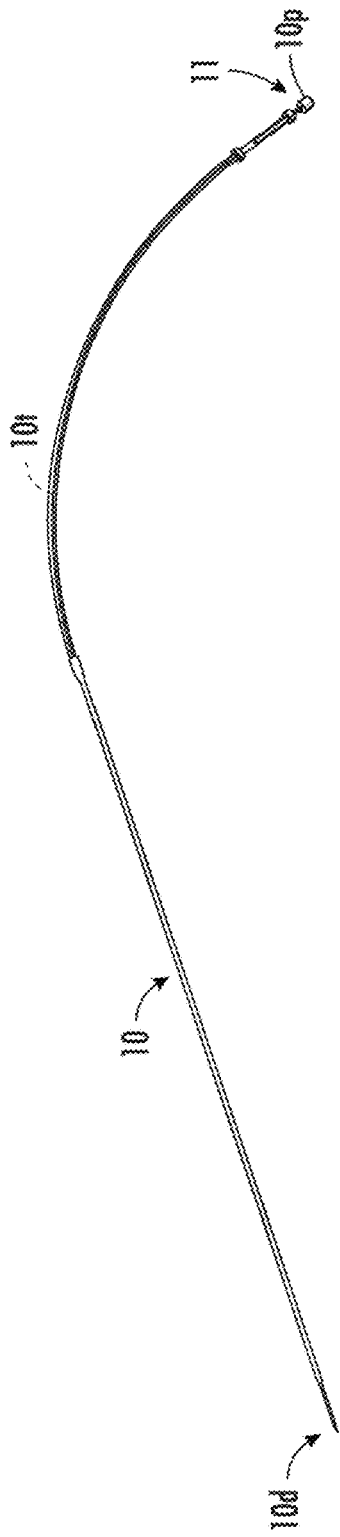
FIG. 1 is a top perspective view of an example cannula assembly according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The terms "FIG." and "Fig." are used interchangeably with the word "Figure" in the specification and/or figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

The term "about," as used herein with respect to a value or number, means that the value or number can vary by +/−twenty percent (20%).

The term "monolithic" means that the component (e.g., inner capillary tube or needle) is formed of a single uniform material.

The term "MRI visible" means that a device is visible, directly or indirectly, in an MRI image. The visibility may be indicated by the increased SNR of the MM signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MM environment and/or can operate as intended in an MRI environment without generating MR signal artifacts, and, as such, if residing within the high-field strength region of the magnetic field, is typically made of a non-ferromagnetic MM compatible material(s) suitable to reside and/or operate in a high magnetic field environment.

The term "high-magnetic field" refers to field strengths above about 0.5 T (Tesla), typically above 1.0 T, and more typically between about 1.5 T and 10 T.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near "real-time" imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., stylet) and the near RT MR image(s) are generated.

The term "sterile," as used herein, means that a device, kit, and/or packaging meets or exceeds U.S./Federal Drug Administration and/or other regulatory medical/surgical cleanliness guidelines, and typically is free from live bacteria or other microorganisms.

Embodiments of the present invention can be utilized with various diagnostic or interventional devices and/or therapies to any desired internal region of an object using any suitable imaging modality, typically an MRI and/or in an MRI scanner or MM interventional suite. However, CT or other imaging modalities may be used. The object can be any object, and may be particularly suitable for animal and/or human subjects for e.g., animal studies and/or veterinarian or human treatments. Some embodiments deliver therapies to the spine. Some embodiments deliver therapies to treat or stimulate a desired region of the sympathetic nerve chain. Other uses, inside or outside the brain, nervous system or spinal cord, include stem cell placement, gene therapy or drug delivery for treating physiological conditions, chemotherapy, drugs including replicating therapy drugs. Some embodiments can be used to treat tumors.

The term "substance," as used herein, refers to a liquid for treating or facilitating diagnosis of a condition and can include bions, stem cells or other target cells to site-specific regions in the body, such as neurological, nerves or other target sites and the like. In some embodiments, stem cells and/or other rebuilding cells or products can be delivered into spine, brain or cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

The term "fluid" with respect to fluid being withdrawn from a subject refers to soft tissue, foreign matter, biological matter including cellular material and liquid in a subject.

The term "infusion" and derivatives thereof refers to the delivery of a substance (which can be a single substance or a mixture) at a relatively slow rate so that the substance can infuse about a target region. Thus, the term "infusate" refers to a substance so delivered.

The term "semi-rigid" refers to devices that have sufficient rigidity to have a self-supporting fixed shape (typically straight tubular or cylindrical shapes) in the absence of applied bending forces but have sufficient flexibility to be able to bend or deflect without breaking in response to forces applied during insertion into or removal from a trajectory guide (see, for example, 1250t, FIG. 14), then return to its original self-supporting shape upon removal of the applied force(s).

The term "flexible" means that the device(s) does not have sufficient rigidity to have a fixed shape without support and can be rolled, coiled, folded for example.

The subject can be any subject, and may be particularly suitable for animal and/or human subjects for e.g., animal studies and/or veterinarian or human treatments.

Some embodiments aspirate fluid from a target intrabody region such as, for example, a brain. For example, aspiration of fluid from a target structure can debulk it. Debulking the structure can relieve pressure on the surrounding areas. This can be desirable as it can be performed in a less invasive manner than surgical resection. See, U.S. patent application Ser. No. 16/217,222, the contents of which are hereby incorporated by reference as if recited in full herein.

Embodiments of the invention can deliver therapies to the spine.

Embodiments of the invention can deliver therapies to treat or stimulate a desired region of the sympathetic nerve chain. Other uses, inside or outside the brain, nervous system or spinal cord, include stem cell placement, gene therapy or drug delivery for treating physiological conditions, chemotherapy, drugs including replicating therapy drugs. Some embodiments can be used to treat a patient with one or more tumors.

Figure 2:
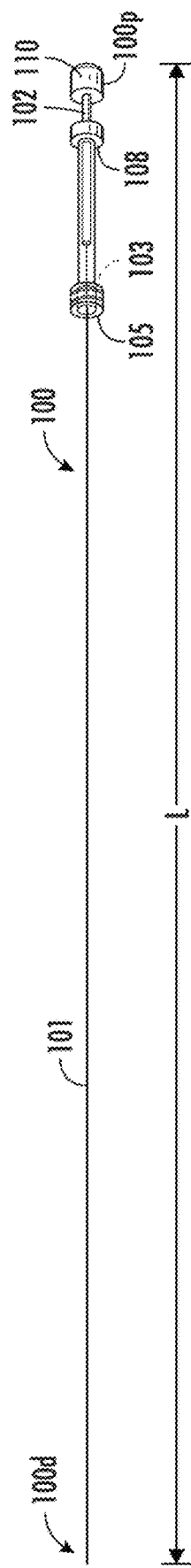
FIG. 2 is a top view of an example plunger assembly according to embodiments of the present invention.
Figure 3:
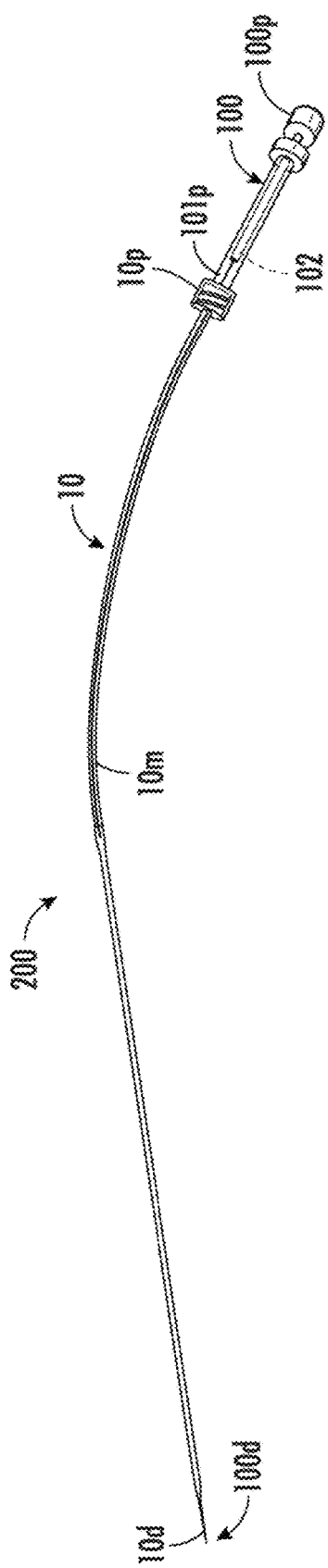
FIG. 3 is an assembled view of the plunger and cannula assemblies shown in FIGS. 1 and 2 forming a fluid transfer assembly according to embodiments of the present invention.

Embodiments of the present invention will now be described in further detail below with reference to the figures. FIG. 1 illustrates an exemplary cannula assembly 10. The cannula assembly 10 is configured for intrabody fluid transfer. FIG. 2 illustrates an exemplary plunger assembly 100. FIG. 3 illustrates the plunger assembly 100 coupled to the cannula assembly 10 to define a transfer assembly 200. When assembled, the plunger assembly 100 extends entirely through the cannula assembly 10. A distal end 100d of the plunger assembly 100 can reside proximate to, such as inward a distance of about 1 mm relative to the distal end 10d, flush with and/or extend out beyond the distal end 10d of the cannula assembly 10 and a proximal end 100p of the plunger assembly 100 extends beyond a proximal end 10p of the cannula assembly 10. The distal end 100d of the plunger assembly 100 can be configured to extend a short distance, such as less than 1 mm, typically such as a distance in a range of about 0-0.5 mm, beyond the distal end 10d of the cannula assembly in a ready to load and/or fully dispensed position. The proximal end 10p of the cannula assembly 10 can comprise a luer connector 11.

In some embodiments, the plunger assembly 100 is configured to cooperate with the cannula assembly 10, allowing the assembled device 200 to be "front loaded". The purpose of front loading the cannula assembly 10 is to load a target fluid into a delivery device to minimize and/or not create any "dead space". The term "dead space" refers to a situation where an undesirable amount of drug is left in a syringe or lumen of the cannula, after a delivery such as an infusion is complete. This can be particularly undesirable where a target drug for delivery is in limited supply such as comprising stem cells and/or where a cell sample obtained from a patient is very small.

Figure 4:
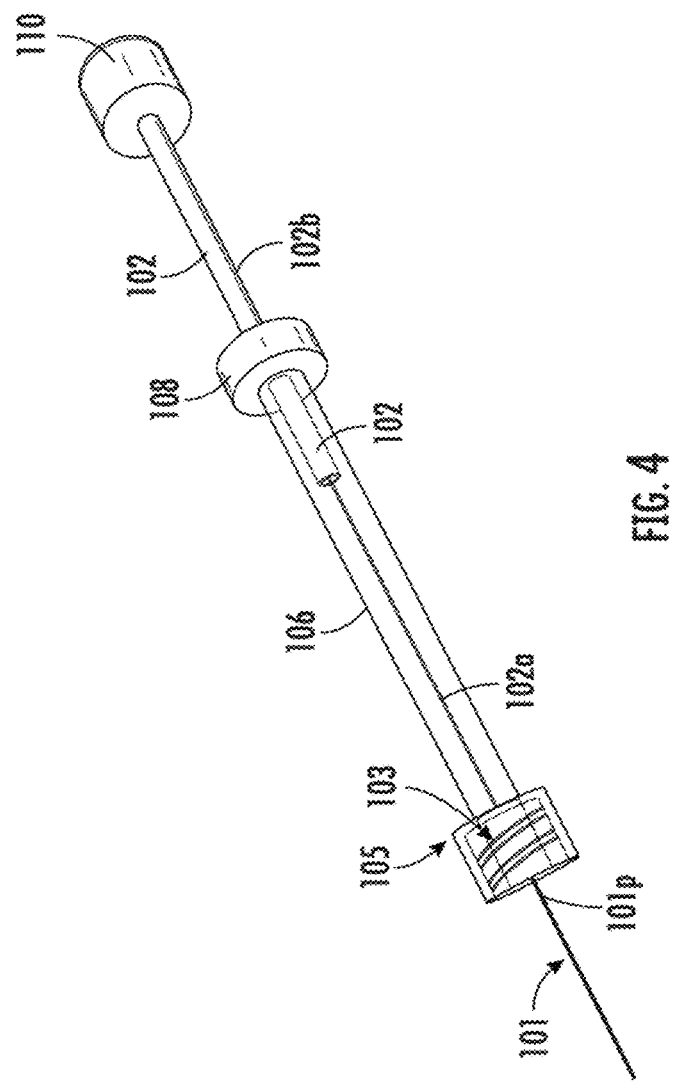
FIG. 4 is an enlarged partial view of a proximal end portion of the assembled components shown in FIG. 3.
Figure 5A:
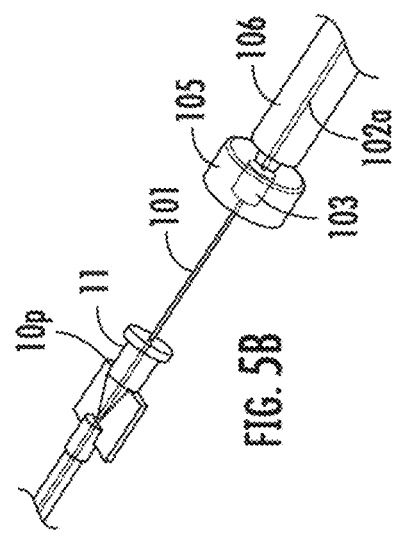
FIG. 5A is a side perspective view of a proximal end portion of the cannula assembly shown in FIG. 1 and a distal end of the plunger assembly shown in FIG. 2 in a first assembly configuration.
Figure 5B:
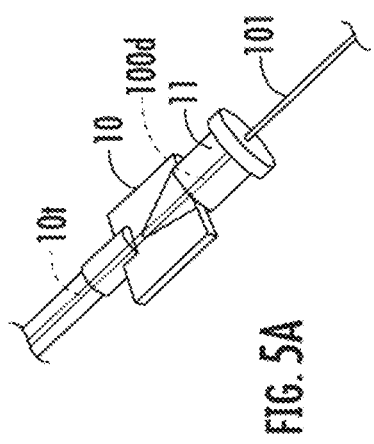
FIG. 5B shows the proximal end portion of the cannula assembly shown in FIG. 5A with the plunger assembly shown in a further assembled state relative to FIG. 5A.

Referring to FIGS. 2-4, as shown, the plunger assembly 100 includes a support body 106 that can optionally be cylindrical (or other shape such as a polygonal or triangular shape) and comprises a luer hub 105 on a distal end thereof. The plunger assembly 100 can also include a plunger support flange 108 on an opposing proximal end.

The plunger assembly 100 can also include a plunger flange 110 that defines the proximal end 100p of the plunger assembly 100.

As is also shown, the plunger assembly 100 comprises a long stylet 101. The long stylet 101 is elongate and has a length L (in a longitudinal direction) that is greater than a length of the support body 106. Typically, the plunger assembly 100 extends an overall length L that can be greater than an overall length L of the cannula assembly 10, such as in a range of about 1 foot to about 10 feet including about 1.5 feet, about 2 feet, about 2.5 feet, about 3 feet, about 3.5 feet, about 4 feet, about 4.5 feet, about 5 feet, about 5.5 feet, about 6 feet, about 6.5 feet, about 7 feet, about 7.5 feet, about 8 feet, about 8.5 feet, about 9 feet, about 9.5 feet and about 10 feet. If sufficiently long, the plunger assembly 100 can be actuated from outside a bore 1350b of a magnet 1350 of an MRI Scanner 1220 (FIG. 13) allowing efficient delivery during an image-guided surgical procedure.

The stylet 101 can be configured to fit any target inner diameter of a respective cannula assembly 10. The plunger assembly 100 can have sufficient flexibility to be able to change in shape from a linear configuration to a curved configuration as shown with respect to FIG. 2 and FIG. 3.

The cannula assembly 10 may have an inner diameter in a range of about 0.008 inches to about 0.021 inches, which may be particularly suitable for certain infusion uses.

When an operator pulls back on the plunger 102, the stylet 101 travels back as well creating a vacuum that evacuates/sucks a fluid such as a drug from a distal end 10d of cannula assembly 10 into the cannula assembly 10 about the stylet 101. Typically, the "front-loaded" drug resides upstream of the distal end 10d of the cannula assembly 10 a distance corresponding to a stroke distance of the plunger 102 and/or a distance in a range of 1 cm to about 30 cm or a range of about 5 cm to about 15 cm. The distance can be, for example, about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, about 26 cm, about 27 cm, about 28 cm, about 29 cm and about 30 cm. The stroke travel distance is below the luer connector 11 and/or luer hub 105 and/or support body 106, more typically between the distal end 10d of the cannula assembly 10 and a medial location 10m of the cannula assembly 10.

When the plunger 102 is moved forward toward the distal end 10d of the cannula assembly 10, the stylet 101 pushes the fluid, e.g., drug, out of the cannula assembly 10 into a target location such as the brain or heart, for example.

Referring to FIGS. 5A, 5B, 6A and 6B, the plunger assembly 100 can attach to the cannula assembly 10 by inserting the stylet 101 into the proximal end 10p of the cannula assembly 10 and threading/pushing the stylet 101 forward to the distal end 10d of the cannula assembly 10, then the plunger assembly 100 can be coupled to (typically locked onto) the cannula assembly 10 at the luer connector 11 (FIG. 6A), similar to a syringe. When fully seated, the distal end 100d of the plunger assembly 100 can reside at a distal end 10d of the cannula assembly 10, and can protrude a distance in a range of about 0-0.5 mm (FIG. 6B) in some particular embodiments.

FIG. 7 illustrates the plunger/cannula assembly 200 in a ready to intake configuration with the plunger flange 110 adjacent the support body flange 108 and the first segment 102a of the plunger 102 having a shorter length inside the support body 106 than the position shown in FIG. 8, with the second segment 102b residing closer to the seal 103 and luer hub 105 in the ready to intake configuration: FIGS. 7, 9A versus the retracted and loaded position shown in FIGS. 8; 9B (the latter having the stylet 101 retracted from the distal end 10d of the cannula assembly).

When in the configuration shown in FIG. 8, the assembly 200 can be inserted through a stereotactic guidance system such as a trajectory guide 1250t (FIG. 14) with the plunger flange 110 accessible to move up and down relative to a patient and the fluid F delivered to or obtained from a patient using the assembly 200.

The plunger assembly 100 can be provided in a kit assembled to the cannula assembly 10.

The plunger assembly 100 can be provided as a separate component in a package with or in a different package from the cannula assembly 10.

The drug can be provided separate from the plunger assembly 10 and/or cannula assembly 100 and is typically loaded onsite prior to delivery.

In some embodiments, for MRI conditional use (safe for use about an MRI Scanner room with magnets generating a magnetic field, but cannot be inserted during active MRI scanning), the stylet 101 can comprise Nitinol wire. In some embodiments, for MRI-safe use (safe for use in an MRI Scanner room even during scanning), the stylet 101 can comprise fused silica.

In some embodiments, for CT or other imaging modalities other materials may be used, preferably biocompatible and inert with respect to the target drug or fluid.

The stylet 101 defines or is attached to a plunger 102. The plunger 102 and stylet 101 are longitudinally extendable and retractable (as a unit/in concert) relative to the cannula assembly 10 and/or a luer hub 105 attached to the plunger assembly 100.

An internal seal 103 can reside at the luer hub 105. The internal seal 103 can define a fluid-tight seal about a segment of the stylet 101 defining a segment of the plunger 102w. The segment of the plunger defined by the stylet 101 can be a small diameter wire 102w.

In some embodiments, at least an elongate segment of the stylet 101 that resides in a distal and medial (intrabody) portion of the cannula assembly 10 can be solid (have a solid core) and have an outer diameter in a range of about 0.005 inches and about 0.020 inches.

The plunger 102 can comprise a first segment 102a that merges into a longitudinally extending second segment 102b. The second segment 102b can have a greater cross-sectional size relative to the first segment 102a inside a support body 106. The second segment 102b can snugly slidably engage the support body 106 but is not required to be fluidly sealed thereto. The support body 106 can be configured to support the plunger 102 including at least part of segments 102a, 102b during actuation to inhibit buckling.

At least a portion of the first segment 102a and a portion of the second segment 102b can reside in the support body 106 when in a fully extended position with the distal end 100d outside the distal end 10d of the cannula assembly (FIGS. 7, 9A) and when in a retracted position for loading/intaking fluid (FIGS. 8, 9B). Thus, the second segment 102b can travel longitudinally with respect to the support body 106 but does not travel below the internal seal 103 and/or luer hub 105 (FIG. 7). The stroke distance "d", between the maximal extended and retracted operative positions, e.g., a location to intake/load fluid relative to a fully assembled position (FIG. 7), can be a distance in a range of about 1 cm to about 30 cm or a range of about 5 cm to about 15 cm, depending on a desired amount of fluid to be loaded into the flow channel 10f of the assembled device 200 (FIGS. 3, 7, 8). The flow channel 10f may have an annular segment defined by the stylet and cannula assembly. The stroke distance can be, for example, about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, about 26 cm, about 27 cm, about 28 cm, about 29 cm and about 30 cm.

The distal end of the stylet 101 can travel 1:1 with the plunger 102 proximal end and pull fluid in to the cannula 10 in a 1:1 ratio, e.g., 1 cm of plunger travel can intake fluid a distance of 1 cm.

The stylet 101 and the cannula assembly 10 can be sized and configured to create a vacuum and intake the fluid using the vacuum to front load the cannula assembly 10. The differential between the inner diameter of the cannula 10 and the outer diameter of the stylet 101 to create a desirable vacuum can be in arrange of about 0.0005 inches and 0.10 inches, for example.

The cannula assembly 10 can comprise an inner tube 10t of continuous length and may have a constant inner diameter, at least over a major portion of a length thereof. In some embodiments, the inner tube can be one continuous piece of material, typically of either PEEK or fused silica glass that extends from the distal end 10d to the connector 11.

Referring to FIG. 1, the stylet 101 can cooperate with the inner tube 10t and define a flow channel 10f (FIG. 9A). The flow channel 10f can have an outer diameter that can be in a range about 0.005 inches and about 0.020 inches, in a range of 100 μm to about 750 μm, such as about 200 μm, or in a range of about 0.20 mm to about 0.05 mm, such as about 0.20 mm or about 0.053 mm.

The inner tube 10*t* can comprise fused silica glass or PEEK or other material. The stylet 101 and inner tube 10*t* can be substantially, if not totally, inert and sterile, so as not to chemically interact with any target fluid in the flow lumen 10*f* (FIG. 9A).

Figure 6A:
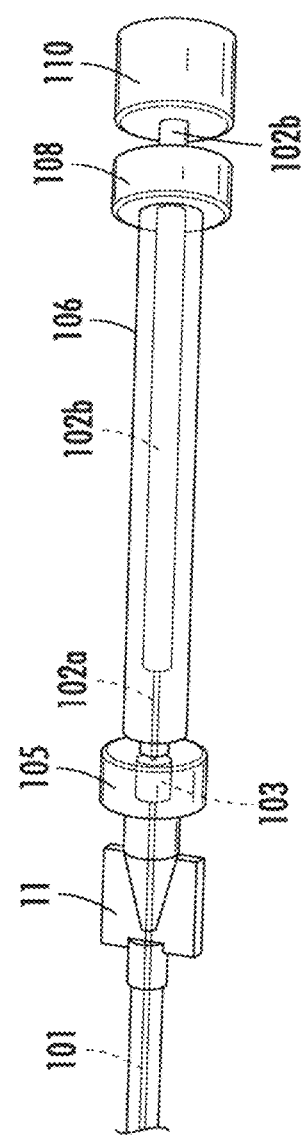
FIG. 6A illustrates the luer connector of the cannula assembly of FIG. 1 attached to the luer connector of the plunger assembly of FIG. 2 after further insertion from the configuration shown in FIG. 5B according to embodiments of the present invention.
Figure 6B:
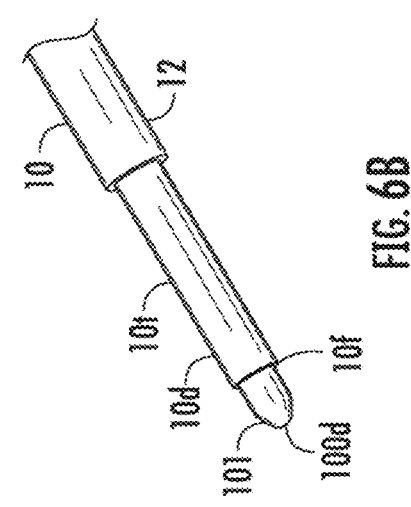
FIG. 6B is a greatly enlarged end perspective view of a distal end of the assembled device shown in FIG. 3.

Referring to FIGS. 1, 6B, 9B, the cannula assembly 10 can comprise an outer tube 12 that can be closely spaced to the inner surface of the outer wall of the inner tube 10*t* to inhibit reverse flow and/or provide a fluid-resistant interface to inhibit flow therebetween.

Figure 10A:
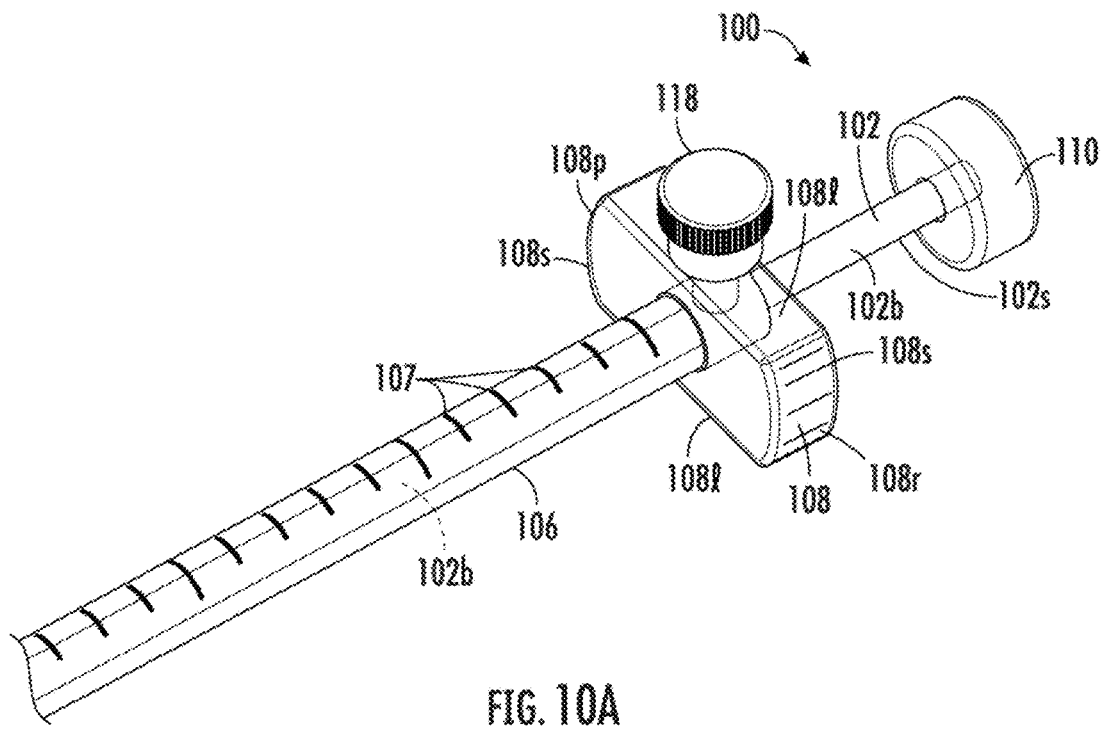
FIG. 10A is an enlarged partial proximal end perspective view of another example of a plunger assembly according to embodiments of the present invention.
Figure 10B:
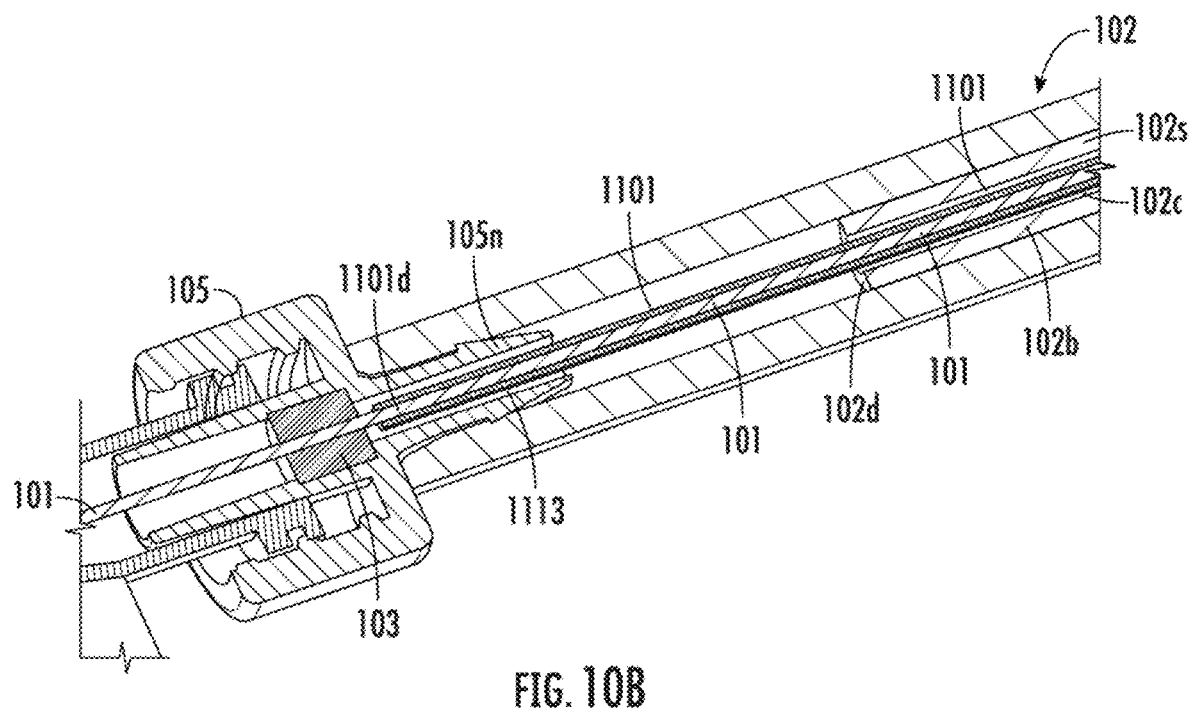
FIG. 10B is a partial section view of an internal interface of support tubing and plunger wire shown in the plunger assembly shown in FIG. 10A according to embodiments of the present invention.
Figure 10C:
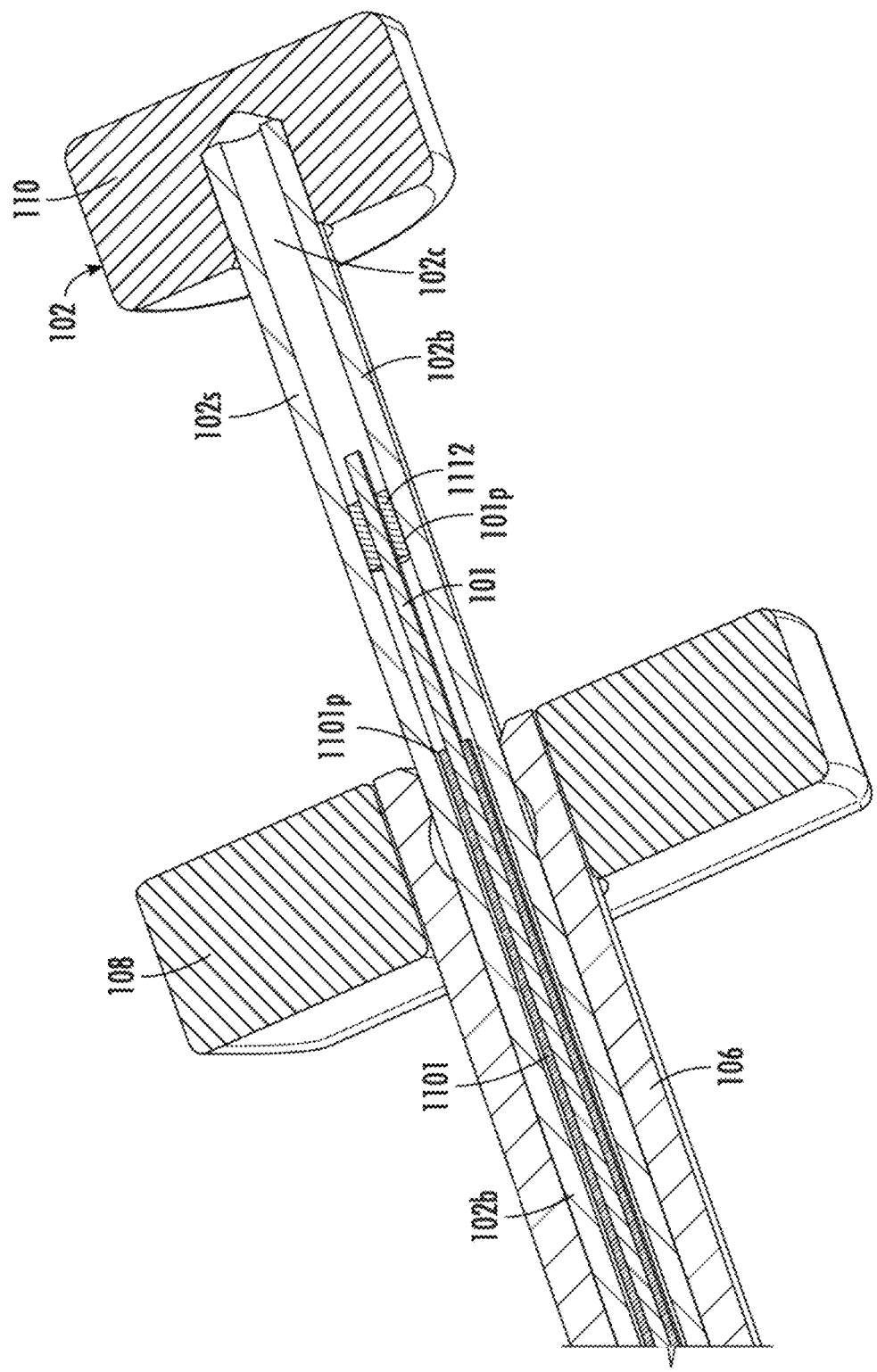
FIG. 10C is a partial section view of the plunger assembly shown in FIG. 10A according to embodiments of the present invention.

Referring to FIG. 10A, the plunger assembly 100 can comprise graduated indicia of depth/distance on the support body 106. The support flange 108 can also include a flange 108 that has an outer perimeter 108*p* with long sides 108*l* connected by shorter sides 108*s*. The shorter sides 108*s* can define finger gripping surfaces. A lock member 118 such as a thumbscrew can be provided on at least one of the long sides 108*l*. The shorter sides 108*s* can be arcuate while the longer sides 108*l* may be planar. The shorter sides 108*s* can comprise ridges 108*r*. The lock member 118 can be configured to directly couple to an outer surface 102*s* of the second segment 102*b* of the plunger 102 inside the support body 106. FIGS. 10B and 10C illustrate that the second segment 102*b* of the plunger 102 can comprise a sleeve 102*s* with a longitudinally extending channel 102*c*. The channel 102*c* can extend above a proximal end portion 101*p* of the stylet 101. The proximal end portion 101*p* of the stylet 101 can be affixed to the channel 102*c* so that the sleeve 102*s* (plunger wire outer body) and style 101 slide in concert.

FIGS. 10B and 10*c* illustrate that the plunger assembly 100 can further include a support tube 1101 that resides between the seal 103 of the luer hub 105 and the plunger flange 110 and encases a portion of the stylet 101. The support tube 1101 can have a distal end portion 1101*d* that resides in an inwardly extending neck 105 of the luer hub 105, axially aligned with the channel 102*c* of the sleeve 102.

As shown in FIG. 10C, a proximal end portion 1101*p* of the support tube 1101 can terminate proximate an outer end of the support flange 108. The support tube 1101 can reside inside the sleeve 102*s* and can terminate short of the proximal end portion 101*p* of the stylet 101. The proximal end portion 101*p* of the style 101 can be affixed to the plunger flange 110 via a bond 1112 inside the channel 102*c* under the flange 110.

The stylet 101 can be configured to slide longitudinally inside the support tube 1101 and the sleeve 102 can slide longitudinally outside the support tube 1101. The support tube 1101 can have a stationary configuration inside the support body 106. At least one end portion of the support tube 1101 can be affixed, such as via a bond 1113, to the support tube 106, shown as indirectly attached to the support tube 106, to anchor the support tube 1101 in a fixed position in the plunger assembly 100.

Figure 11:
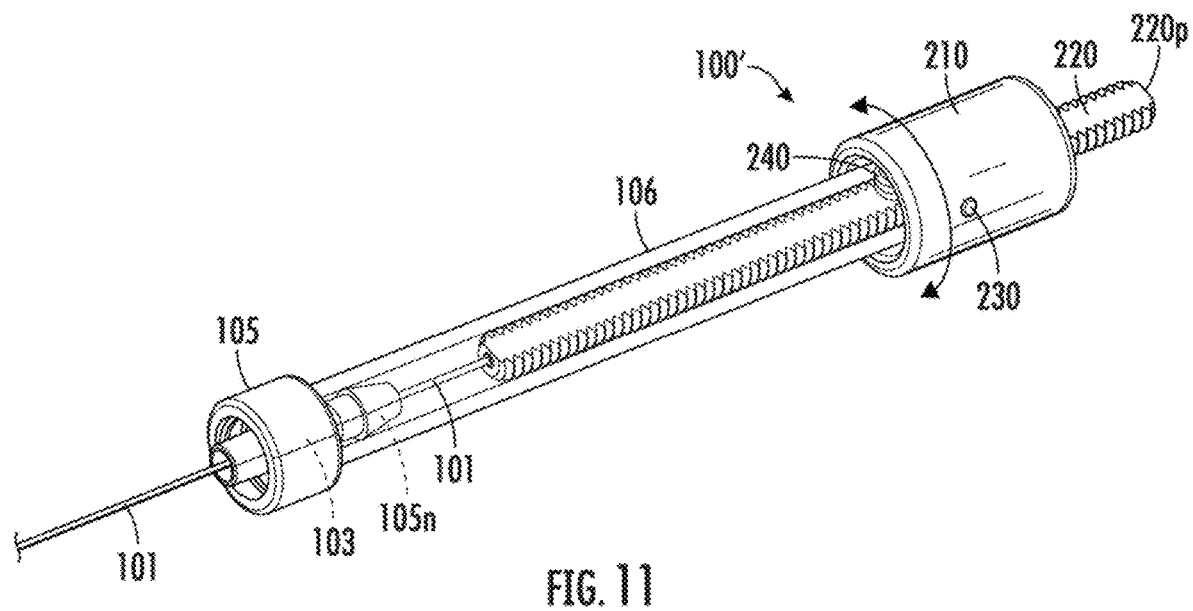
FIG. 11 is an enlarged partial perspective view of another embodiment of a plunger assembly according to embodiments of the present invention.
Figure 12:
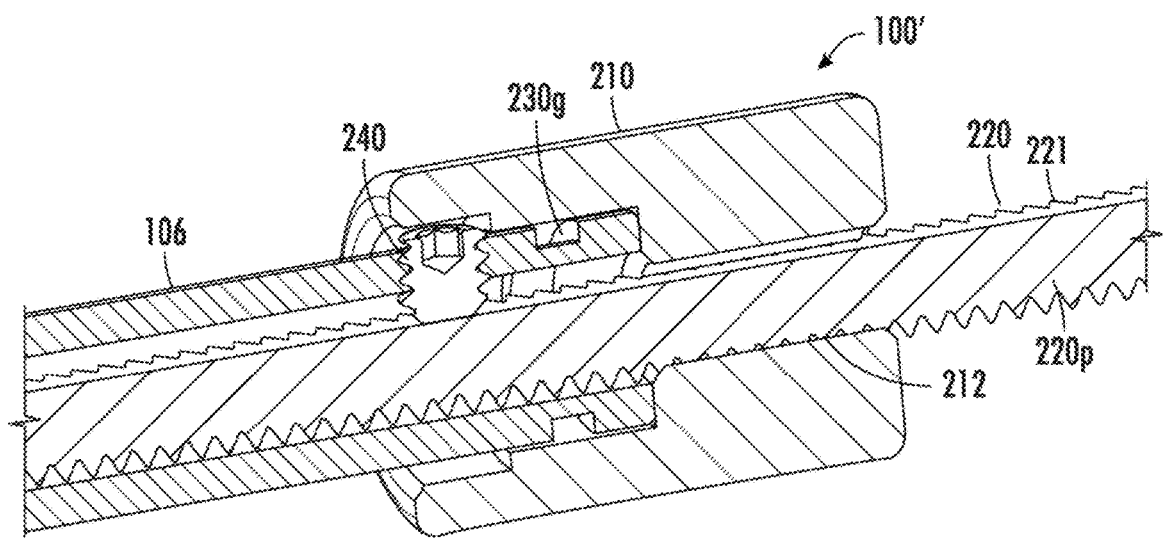
FIG. 12 is a greatly enlarged section view of a segment of the proximal end portion of the plunger assembly shown in FIG. 11.

Turning now to FIGS. 11 and 12, another embodiment of a plunger assembly 100' is shown. In this embodiment, a drive screw 220 can be used to translate the stylet 101 instead of a plunger 102, which may provide for increased precision over manual plunger operation using the plunger flange. The stylet 101 can be attached to the drive screw 220 inside the support body 106, above the luer hub 105 with the seal 103. The plunger assembly 100' can include a collar 210 that is affixed to the screw 220. Rotation of the collar 210 can translate the drive screw 220, which retracts or extends the stylet 101.

One full rotation of the collar 210 can translate the stylet 101 a defined distance, such as a distance in a range of about 0.1 mm and about 2 mm. In some embodiments, one rotation of the collar 210 can be configured to provide about 1 mm of longitudinal travel (retraction and extension) of the stylet 101.

The stylet 101 can be affixed to the drive screw 220. The proximal end portion 101*p* of the stylet can extend into a channel in the screw 220. The proximal end portion 101*p* of the stylet 101 can be bonded to the screw 220.

The collar 210 can be fixed to the support body 106. A set screw 240 can thread into the support body 106. The set screw 240 can prevent the drive screw 220 from rotating inside the collar 210.

A dowel pin 230 can engage an interior groove 230*g* in the collar 210 to keep the collar 210 assembled to the support body 106 and/or prevent the drive screw 220 from rotating. The collar 210 can have internal threads 212 that engage the threads 221 of the drive screw 220.

A proximal end portion 220*p* of the drive screw 220 can extend out of the collar 210. The threads 212 can extend over a sub-length of the collar 210 inside the collar 210.

Although not shown, the support tube 1101 discussed above, can be provided in the support body 106, under the drive screw 220.

Figure 14:
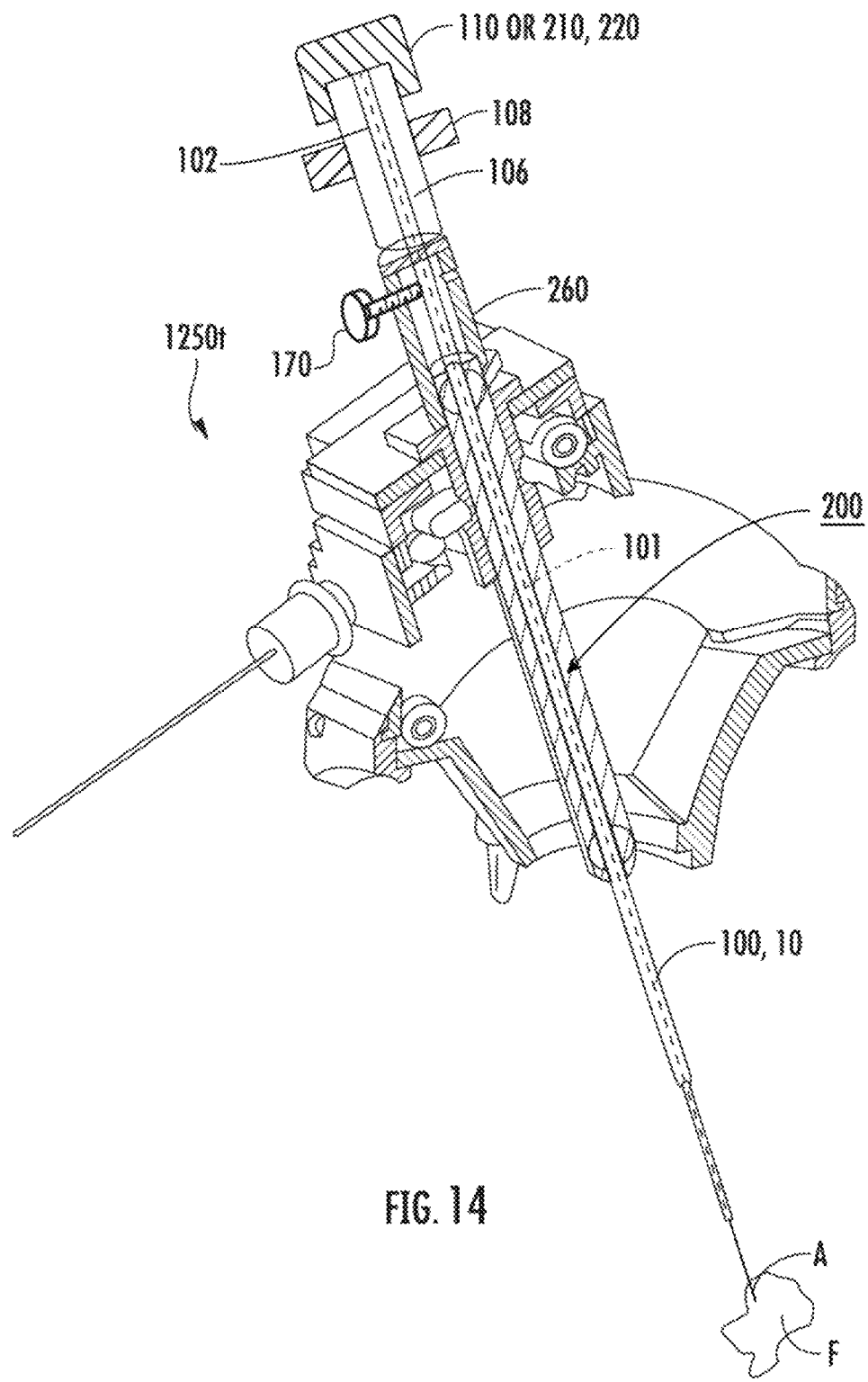
FIG. 14 is an enlarged partial section view of an example cannula and plunger assembly shown in FIG. 3, held by a trajectory guide for intrabody placement according to embodiments of the present invention.
Figure 5:
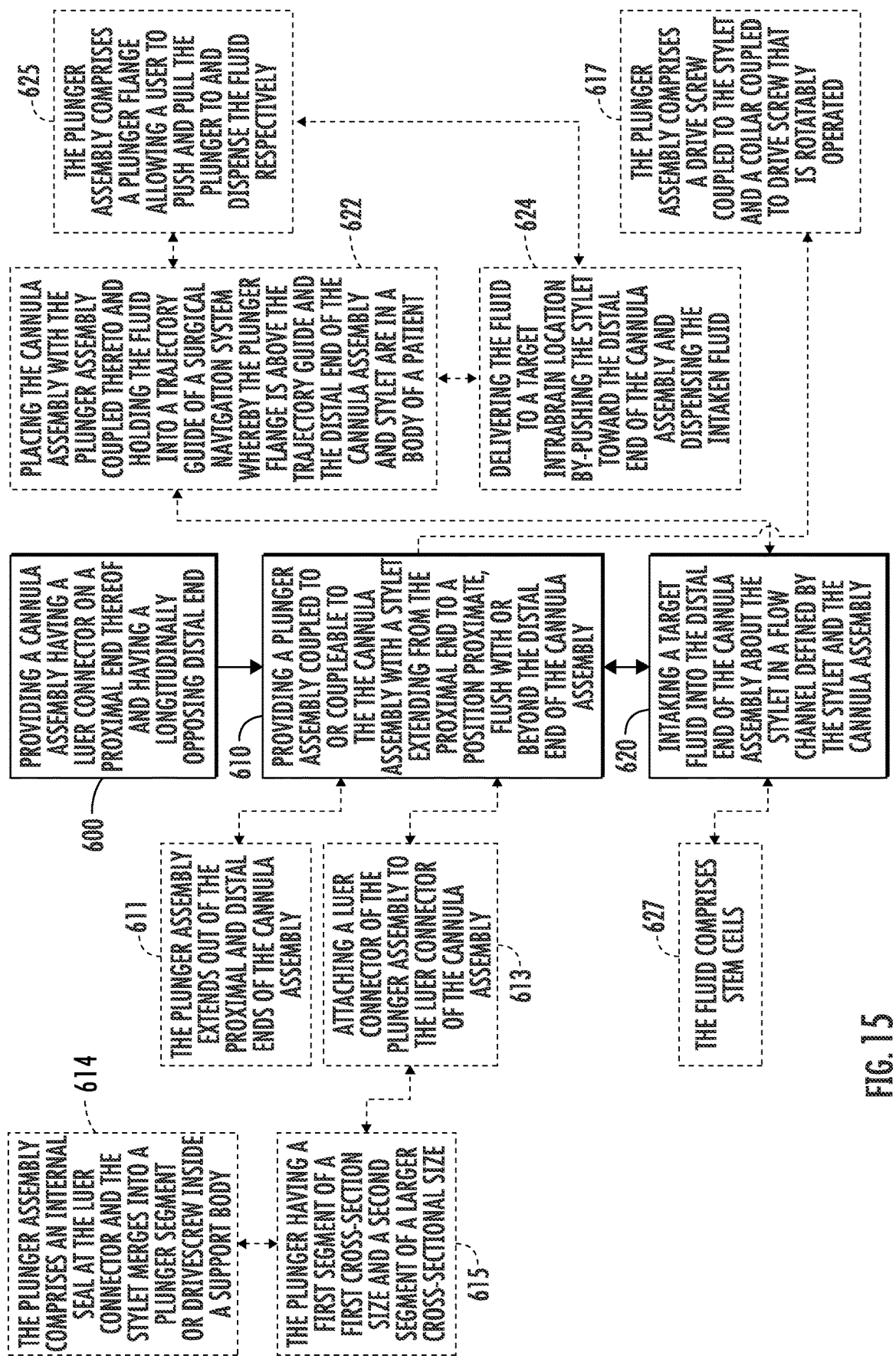

Referring to FIG. 14, the assembly 200 can extend through a tubular support 260 of a trajectory guide 1250*t* that can be held by a base or frame e.g., a stereotactic frame that can be secured to the patient or that can be secured to a holder residing over the patient. A lock 170 can be used to secure the assembly 200 at a desired position in the tubular support 260 to place the distal end 10*d* at a target region A and withdraw or delivery substance F. See, e.g., U.S. Pat. Nos. 8,315,689, 8,175,677 and 8,374,677 and US Patent Application Publication No. 2010/0198052 (Ser. No. 12/694,865) for descriptions of patient planning and entry protocols and frames and trajectory guides, the contents of which are hereby incorporated by reference as if recited in full herein.

Figure 13:
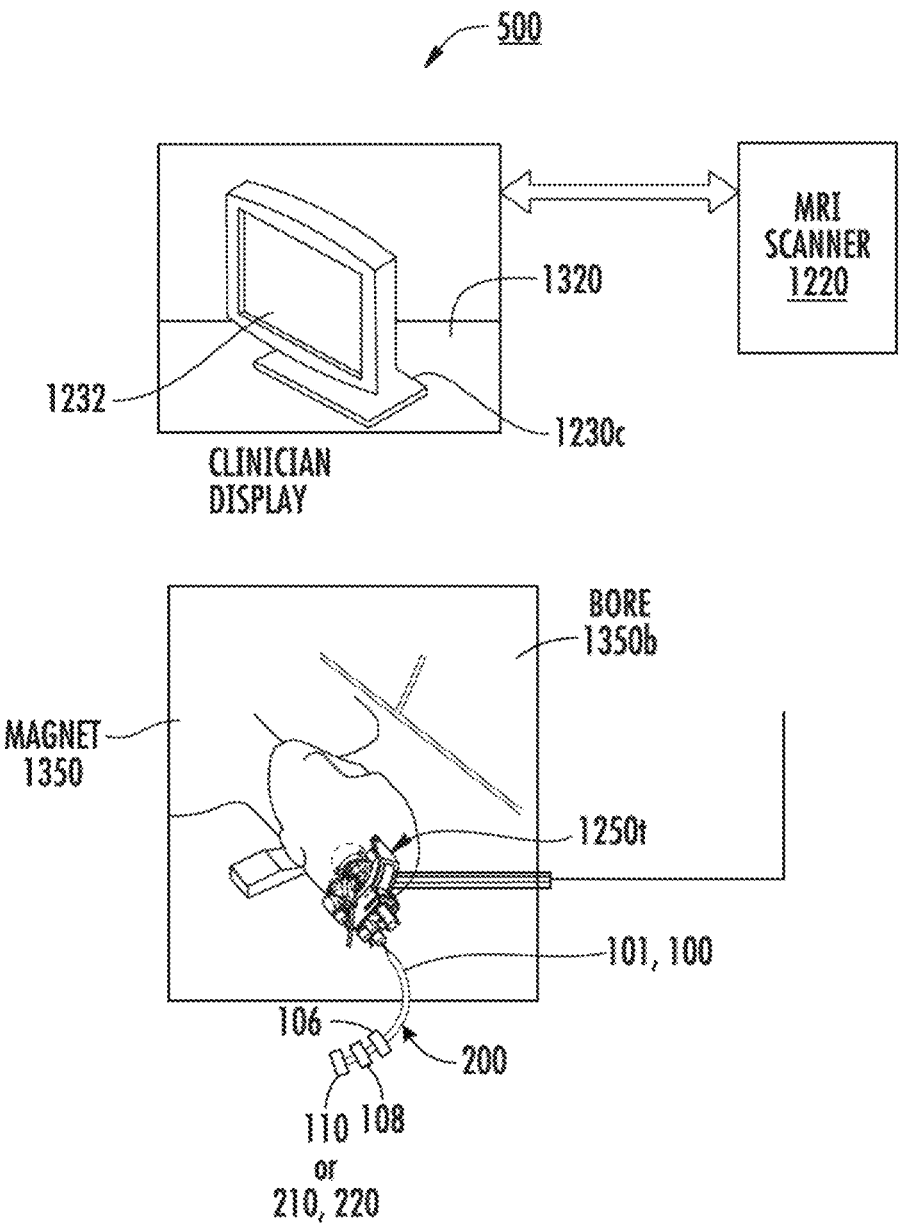
FIG. 13 is a schematic illustration of a medical intrabody fluid transfer system operable in an image guided surgical navigation system according to embodiments of the present invention.

FIG. 13 illustrates an MRI-guided interventional system 500 with an MRI scanner 1220, a clinician workstation 1230 with at least one circuit 1230*c*, at least one display 1232, an MRI compatible trajectory guide 1250*t* and a fluid transfer assembly 200. The system 500 can be configured to render or generate near real time or real time visualizations of the target anatomical space using MM image data and predefined data of at least one surgical tool (e.g., tubular cannula 20 and/or trajectory guide 1250*t*) to segment the image data and place the trajectory guide 1250*t* and the cannula 20 in the rendered visualization in the correct orientation and position in 3D space (which is the MM surgical space for MM embodiments), anatomically registered to a patient. The trajectory guide 1250*t* and the cannula 20 can include or cooperate with tracking, monitoring and/or other interventional components.

The trajectory guide 1250*t* can be configured to provide one or more of an X-Y adjustment and/or pitch and roll adjustment in order to accurately position the assembly 200 at a desired location within a patient. For additional discussion of examples of suitable trajectory guides, see U.S. Pat. No. 8,374,677, the contents of which are hereby incorporated by reference as if recited in full herein. However, it is noted that other trajectory guide configurations may be used and embodiments of the invention are not limited by the examples of the trajectory guides herein.

According to some embodiments, the systems are configured to provide a substantially automated or semi-automated and relatively easy-to-use MRI-guided system with defined workflow steps and interactive visualizations. In particular embodiments, the systems define and present workflow with discrete steps for finding target and entry point(s), guiding the alignment of the targeting cannula to a planned trajectory, monitoring the insertion of the cannula assembly 200, and adjusting the (X-Y) position in cases where the placement needs to be corrected. During steps where specific MR scans are used, the circuit or computer module can display data for scan plane center and angulation to be entered at the console. The workstation/circuit can passively or actively communicate with the MR scanner. The system can also be configured to use functional patient data (e.g., fiber tracks, fMRI and the like) to help plan or refine a target surgical site and/or access path.

The system 500 may also include a decoupling/tuning circuit that allows the system to cooperate with the MRI scanner 1220 and filters and the like. See, e.g., U.S. Pat. Nos. 6,701,176; 6,904,307 and U.S. Patent Application Publication No. 2003/0050557, the contents of which are hereby incorporated by reference as if recited in full herein.

The assembly 200 can be configured to flowably introduce, infuse and/or inject a desired therapy substance (e.g., antigen, gene therapy, chemotherapy or stem-cell or other therapy type).

In some embodiments, the intrabody fluid transfer assembly 200 is configured to deliver a drug therapy to the brain. The drug therapy can comprise substance F delivered to the target site or region A (FIG. 14) through the fluid/flow channel 10*f* (FIG. 6B) and may be any suitable and desired substance for drug discovery, animal or human clinical trials and/or approved medical procedures. According to some embodiments, the substance F is a liquid or slurry. In the case of a tumor, the substance may be a chemotherapeutic (cytotoxic) fluid. In some embodiments, the substance can include certain types of advantageous cells that act as vaccines or other medicaments (for example, antigen presenting cells such as dendritic cells). The dendritic cells may be pulsed with one or more antigens and/or with RNA encoding one or more antigen. Exemplary antigens are tumor-specific or pathogen-specific antigens. Examples of tumor-specific antigens include, but are not limited to, antigens from tumors such as renal cell tumors, melanoma, leukemia, myeloma, breast cancer, prostate cancer, ovarian cancer, lung cancer and bladder cancer. Examples of pathogen-specific antigens include, but are not limited to, antigens specific for HIV or HCV. In some embodiments, the substance F may comprise radioactive material such as radioactive seeds. Substances F delivered to a target area in accordance with embodiments of the present invention may include, but are not limited to, the following drugs (including any combinations thereof) listed in Table 1:

TABLE 1

| DRUG (generic name) | DISORDER(S) |
|---|---|
| Caprylidene | Alzheimer's disease |
| Donepezil | Alzheimer's disease |
| Galantamine | Alzheimer's disease |
| Memantine | Alzheimer's disease |
| Tacrine | Alzheimer's disease |
| vitamin E | Alzheimer's disease |
| ergoloid mesylates | Alzheimer's disease |

TABLE 1-continued

| DRUG (generic name) | DISORDER(S) |
|---|---|
| Riluzole | Amyotrophic lateral sclerosis |
| Metoprolol | Benign essential tremors |
| Primidone | Benign essential tremors |
| Propanolol | Benign essential tremors |
| Gabapentin | Benign essential tremors & Epilepsy |
| Nadolol | Benign essential tremors & Parkinson's disease |
| Zonisamide | Benign essential tremors & Parkinson's disease |
| Carmustine | Brain tumor |
| Lomustine | Brain tumor |
| Methotrexate | Brain tumor |
| Cisplatin | Brain tumor & Neuroblastoma |
| Ioversol | Cerebral arteriography |
| Mannitol | Cerebral Edema |
| Dexamethasone | Cerebral Edema & Neurosarcoidosis |
| Baclofen | Cerebral spasticity |
| Ticlopidine | Cerebral thrombosis/embolism |
| Isoxsuprine | Cerebrovascular insufficiency |
| Cefotaxime | CNS infection & Meningitis |
| Acyclovir | Encephalitis |
| Foscarnet | Encephalitis |
| Ganciclovir | Encephalitis |
| interferon alpha-2a | Encephalitis |
| Carbamazepine | Epilepsy |
| Clonazepam | Epilepsy |
| Diazepam | Epilepsy |
| divalproex sodium | Epilepsy |
| Ethosuximide | Epilepsy |
| Ethotoin | Epilepsy |
| Felbamate | Epilepsy |
| Fosphenytoin | Epilepsy |
| Levetiracetam | Epilepsy |
| Mephobarbital | Epilepsy |
| Paramethadione | Epilepsy |
| Phenytoin | Epilepsy |
| Trimethadione | Epilepsy |
| Pregabalin | Epilepsy & Neuralgia |
| immune globulin intravenous | Guillain-Barre Syndrome |
| interferon beta-1b | Guillain-Barre Syndrome & Multiple sclerosis |
| Azathioprine | Guillain-Barre Syndrome & Multiple sclerosis & Neurosarcoidosis |
| Risperidone | Head injury |
| Tetrabenazine | Huntington's disease |
| Acetazolamide | Hydrocephalus & Epilepsy |
| Alteplase | Ischemic stroke |
| Clopidogrel | Ischemic stroke |
| Nimodipine | Ischemic stroke & Subarachnoid hemorrhage |
| Aspirin | Ischemic stroke & Thromboembolic stroke |
| Amikacin | Encaphalitis |
| Ampicillin | Encaphalitis |
| ampicillin/sulbactam | Encaphalitis |
| Ceftazidime | Encaphalitis |
| Ceftizoxime | Encaphalitis |
| Cefuroxime | Encaphalitis |
| Chloramphenicol | Encaphalitis |
| cilastatin/imipenem | Encaphalitis |
| Gentamicin | Encaphalitis |
| Meropenem | Encaphalitis |
| Metronidazole | Encaphalitis |
| Nafcillin | Encaphalitis |
| Oxacillin | Encaphalitis |
| Piperacillin | Encaphalitis |
| Rifampin | Encaphalitis |
| sulfamethoxazole/trimethoprim | Encaphalitis |
| Tobramycin | Encaphalitis |
| Triamcinolone | Encaphalitis |
| Vancomycin | Encaphalitis |
| Ceftriaxone | Encaphalitis & Neurosyphilis |
| Penicillin | Encaphalitis & Neurosyphilis |
| Corticotrophin | Multiple sclerosis |
| Dalfampridine | Multiple sclerosis |
| Glatiramer | Multiple sclerosis |
| Mitoxantrone | Multiple sclerosis |
| Natalizumab | Multiple sclerosis |
| Modafinil | Multiple sclerosis |
| Cyclophosphamide | Multiple sclerosis & Brain tumor & Neuroblastoma |

TABLE 1-continued

| DRUG (generic name) | DISORDER(S) |
| --- | --- |
| interferon beta-1a | Multiple sclerosis & Neuritis |
| Prednisolone | Multiple sclerosis & Neurosarcoidosis |
| Prednisone | Multiple sclerosis & Neurosarcoidosis |
| Amantadine | Multiple sclerosis & Parkinson's disease |
| Methylprednisolone | Neuralgia |
| Desvenlafaxine | Neuralgia |
| Nortriptyline | Neuralgia |
| Doxorubicin | Neuroblastoma |
| Vincristine | Neuroblastoma |
| Albendazole | Neurocystecercosis |
| chloroquine phosphate | Neurosarcoidosis |
| Hydroxychloroquine | Neurosarcoidosis |
| Infliximab | Neurosarcoidosis |
| Pentoxyfilline | Neurosarcoidosis |
| Thalidomide | Neurosarcoidosis |
| Apomorphine | Parkinson's disease |
| Belladonna | Parkinson's disease |
| Benztropine | Parkinson's disease |
| Biperiden | Parkinson's disease |
| Bromocriptine | Parkinson's disease |
| Carbidopa | Parkinson's disease |
| carbidopa/entacapone/levodopa | Parkinson's disease |
| carbidopa/levodopa | Parkinson's disease |
| Entacapone | Parkinson's disease |
| Levodopa | Parkinson's disease |
| pergolide mesylate | Parkinson's disease |
| Pramipexole | Parkinson's disease |
| Procyclidine | Parkinson's disease |
| Rasagiline | Parkinson's disease |
| Ropinirole | Parkinson's disease |
| Rotiotine | Parkinson's disease |
| Scopolamine | Parkinson's disease |
| Tolcapone | Parkinson's disease |
| Trihexyphenidyl | Parkinson's disease |
| Seleginline | Parkinson's disease |
| Rivastigmine | Parkinson's disease & Alzheimer's disease |
| Anisindione | Thromboembolic stroke |
| Warfarin | Thromboembolic stroke |
| 5-hydroxytryptophan | Depression & Anxiety & ADHD |
| Duloxetine | Depression & Anxiety & Bipolar disorder |
| Escitalopram | Depression & Anxiety & Bipolar disorder |
| Venlafaxine | Depression & Anxiety & Bipolar disorder & Autism & Social anxiety disorder |
| Desvenlafaxine | Depression & Anxiety & PTSD & ADHD |
| Paroxetine | Depression & Anxiety & PTSD & Social anxiety disorder |
| fluoxetine/olanzapine | Depression & Bipolar disorder |
| 1-methylfolate | Depression & BPD |
| Amitriptyline | Depression & PTSD |
| Sertraline | Depression & PTSD & Bipolar disorder & Social anxiety disorder |
| Fluvoxamine | Depression & PTSD & Social anxiety disorder |
| Olanzapine | Depression & Schizophrenia & Bipolar disorder |
| Paliperidone | Depression & Schizophrenia & Bipolar disorder |
| Aripiprazole | Depression & Schizophrenia & Bipolar disorder & Autism |
| Quetiapine | Depression & Schizophrenia & PTSD & BPD & Bipolar disorder |
| Risperidone | Depression & Schizophrenia & PTSD & BPD & Bipolar disorder & Autism |
| Amisulpride | Depression & Social anxiety disorder |
| Chlorpromazine | Psychosis |
| Droperidol | Psychosis |
| Fluphenazine | Psychosis |
| Periciazine | Psychosis |
| Perphenazine | Psychosis |
| Thiothixene | Psychosis |
| Triflupromazine | Psychosis |
| Haloperidol | Psychosis & Dementia |
| Prazosin | PTSD |
| Clozapine | Schizophrenia |
| Flupenthixol | Schizophrenia |
| Iloperidone | Schizophrenia |
| Loxapine | Schizophrenia |
| Mesoridazine | Schizophrenia |
| Promazine | Schizophrenia |
| Reserpine | Schizophrenia |
| Thioridazein | Schizophrenia |
| Zuclopenthixol | Schizophrenia |
| Asenapine | Schizophrenia & Bipolar disorder |
| Levomepromazine | Schizophrenia & Bipolar disorder |
| Ziprasidone | Schizophrenia & Bipolar disorder |
| Molindone | Schizophrenia & Psychosis |
| Pimozide | Schizophrenia & Psychosis |
| Thioridazine | Schizophrenia & Psychosis |
| Cytarabine | Chemotherapy, hematological malignancies |

According to some embodiments, the intrabody fluid transfer system 200 can be configured as an infusate delivery system that is delivered to a patient at an infusion rate in the range of from about 1 µL/minute to about 3 µL/minute.

Insertion of the surgical cannula assembly 200 (or any other surgical, e.g., delivery, cannula) can be tracked in near real time by reference to a void in the patient tissue caused by the surgical cannula assembly 200 and reflected in the MR image. In some embodiments, one or more MRI-visible fiducial markers may be provided on the surgical tubular cannula 10, MR scanned and processed, and displayed on the UI. In some embodiments, components of the surgical cannula assembly 200 may itself be formed of an MRI-visible material, MR scanned and processed, and displayed on the UI.

According to some embodiments, the surgical cannula/plunger assembly 200 may include an embedded intrabody MRI antenna (not shown) that is configured to pick-up MRI signals in local tissue during an MRI procedure. The MM antenna can be configured to reside on a distal end portion of the surgical cannula. In some embodiments, the antenna has a focal length or signal-receiving length of between about 1-5 cm, and typically is configured to have a viewing length to receive MRI signals from local tissue of between about 1-2.5 cm. The MRI antenna can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. 2003/0050557; 2004/0046557; and 2003/0028095, the contents of which are also hereby incorporated by reference as if recited in full herein.

While the devices have been described by way of example as delivery devices and methods for delivering a substance to a patient, in accordance with some embodiments of the invention, the devices can be used to withdraw and/or aspirate a substance (e.g., spinal fluid, cardiac fluid or neuro fluid) from a patient. Thus, it will be appreciated that the devices and methods as disclosed herein can be used to transfer a substance into and/or from a patient.

While the devices have been described herein primarily with reference to MRI-guided insertion and infusion procedures, in some embodiments the devices can be used in procedures without MRI guidance, such as using other imaging modalities, such as, but not limited to, CT imaging systems, where image-guided surgical navigation is desired.

While the cannula/plunger assembly 200 has been described with the surgical assembly 200 coupled to a trajectory guide 1250t, other types of trajectory guidance or stereotactic frames or without a stereotactic frame or trajectory guide.

FIG. 15 is a flow chart of exemplary actions that can be carried out according to embodiments of the present invention. A cannula assembly having a luer connector on a proximal end thereof and having a longitudinally opposing distal end is provided (block 600). A plunger assembly that is coupleable to or coupled to the cannula assembly is provided. The plunger assembly comprises a stylet extending from the proximal end to a position proximate, flush with or beyond the distal end of the cannula assembly (block 610). A target fluid is intaken into the distal end of the cannula assembly about the stylet in a fluid/flow channel created/defined by the stylet and the cannula assembly (block 620). The cannula assembly and the plunger assembly can cooperate to generate a vacuum that causes the fluid to be intaken into the distal end portion and upstream thereof (but typically below the plunger luer hub).

The plunger assembly can comprise a drive screw residing at least partially inside a support body and coupled to the stylet and a collar rotatably coupled to the drive screw configured to retract and extend the stylet (block 617).

The cannula assembly with the plunger assembly coupled thereto and holding the fluid can be placed into a trajectory guide of a surgical navigation system whereby the plunger flange is above the trajectory guide and the distal end of the cannula assembly and stylet are in a body of a patient (block 622).

The fluid can be delivered to a target intrabrain location by pushing a plunger toward the distal end of the cannula assembly and dispensing the intaken fluid (block 624).

The plunger assembly comprises a plunger flange allowing a user to push and pull the plunger to intake and dispense the fluid (block 625).

The plunger assembly is configured to extend to (concurrently) extend out of the proximal and distal ends of the cannula assembly (block 611) (during at least the delivery/dispensing operation).

A luer connector of the plunger assembly can be connected to the luer connector of the cannula assembly (block 613).

The plunger assembly comprises an internal seal at the luer connector and the stylet merges into a plunger segment or drive screw inside a support body (block 614).

The plunger segment can have a first segment of a first cross-section size and a second segment of a larger cross-sectional size, optionally the first segment is a stylet and the second segment can be defined by a sleeve affixed to the stylet (block 615).

The fluid comprises stem cells (block 627).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An intrabody fluid transfer system comprising:
a cannula assembly comprising a proximal end with a luer connector and having a longitudinally opposing distal end with an open channel extending therethrough; and
a plunger assembly coupled to the cannula assembly, the plunger assembly comprising a stylet that extends in the open channel of the cannula assembly to position a distal end of the stylet adjacent the distal end of the cannula assembly, wherein the open channel and the stylet cooperate to define a fluid channel, and wherein the stylet provides or is attached to a drive member of the plunger assembly to controllably retract and extend the stylet relative to the cannula assembly whereby longitudinal retraction of the stylet in the open channel of the cannula assembly creates a vacuum sufficient to front-load fluid into the open channel at the distal end of the cannula assembly.

2. The intrabody fluid transfer system of claim 1, wherein, with the stylet in a first position associated with a ready to intake fluid or a fully injected position, the distal end of the stylet extends flush with or out of the distal end of the cannula assembly.

3. The intrabody fluid transfer system of claim 1, wherein, fluid is held for dispensing to a patient only in the fluid channel, and wherein the fluid channel is only at a location between the distal end of the cannula assembly and a medial portion of the cannula assembly.

4. The intrabody fluid transfer system of claim 1, wherein the plunger assembly further comprises a luer connector comprising an internal seal that defines a fluid-tight seal for a segment of the stylet, wherein the luer connector of the plunger assembly is attached to the luer connector of the cannula assembly; and
a support body coupled to the luer connector of the plunger assembly and extending above the distal end of the stylet, wherein the support body surrounds a sub-segment of the stylet.

5. The intrabody fluid transfer system of claim 4, further comprising a plunger that defines the drive member whereby the plunger and stylet move in concert and as a unit, the plunger comprising a first segment coupled to or defined by the stylet and a second segment having a greater cross-sectional size that the first segment, wherein the second segment merges into an external plunger flange, wherein the support body encloses the first segment and at least a portion of the second segment and the first segment and the second segment are longitudinally movable relative to the support body, and wherein with the plunger in a first position, the second segment resides closer to the luer connector of the plunger assembly and the luer connector of the cannula assembly than in a second position.

6. The intrabody fluid transfer system of claim 1, further comprising a drive screw that defines the drive member.

7. The intrabody fluid transfer system of claim 6, further comprising a collar that is coupled to a support and the drive screw, wherein the support body is coupled to the luer connector of the plunger assembly and surrounds a sugsegment of the style, and wherein the collar is rotatable in clockwise and counterclockwise directions to translate the stylet.

8. The intrabody fluid transfer system of claim 4, further comprising a support tube residing inside the support body and that is coupled to the luer connector of the plunger assembly above the internal seal, wherein the stylet is slidably coupled to the support tube to retract and extend inside the support tube while the support body slidably retracts and extends in concert with the stylet about an outer wall of the support tube.

9. The intrabody fluid transfer system of claim 4, wherein the stylet has a length outside the support body that is in a range of 6 inches and 10 feet.

10. The intrabody fluid transfer system of claim 1, wherein the stylet comprises an MRI compatible material and has a maximal outer diameter in a range of about 0.005 inches and about 0.020 inches.

11. The intrabody fluid transfer system of claim 1, wherein the stylet comprises Nitinol.

12. The intrabody fluid transfer system of claim 1, wherein the stylet comprises fused silica.

13. The intrabody fluid transfer system of claim 1, wherein the fluid channel has a length in a range of about 1 cm to about 30 cm.

14. An intrabody fluid medication system comprising:
a cannula assembly comprising a proximal end with a luer connector and having a longitudinally opposing distal end with an open channel extending therethrough;
a plunger assembly coupled to the cannula assembly, the plunger assembly comprising a drive member and a stylet, wherein the stylet resides at least partially in the open channel of the cannula assembly to position a distal end of the stylet adjacent the distal end of the cannula assembly, wherein the open channel and the stylet cooperate to generate a vacuum to intake fluid into a fluid holding channel that is only between the distal end of the cannula assembly and a medial portion of the cannula assembly; and
a fluid medication held in the fluid holding channel for delivery to a patient,
wherein the drive member and the stylet move in concert over a defined stroke distance to retract in the open channel and intake the fluid medication into the fluid holding channel then move in concert a reverse direction to deliver the fluid medication from the fluid holding channel.

15. The intrabody fluid medication system of claim 14, wherein the drive member is a plunger.

16. The intrabody fluid medication system of claim 14, wherein the cannula assembly that surrounds a distal end portion of the stylet and the stylet have a clearance therebetween that is in a range of 0.00005 inches and 0.10 inches.

17. The intrabody fluid medication system of claim 14, further comprising an internal seal that resides above the fluid holding channel and defines a fluid tight seal between a segment of the stylet and the cannula assembly.

* * * * *

UNITED STATES PATENT AND TRADEMARK OFFICE
CERTIFICATE OF CORRECTION

PATENT NO. : 11,707,569 B2
APPLICATION NO. : 17/032140
DATED : July 25, 2023
INVENTOR(S) : Daly et al.

It is certified that error appears in the above-identified patent and that said Letters Patent is hereby corrected as shown below:

In the Specification

Column 2, Line 30: delete "MM" and insert --MRI--

Column 6, Line 9: delete "MM" and insert --MRI--

Column 6, Line 16: delete "MM" and insert --MRI--

Column 6, Line 20: delete "MM" and insert --MRI--

Column 6, Line 63: delete "MM" and insert --MRI--

Column 12, Line 50: delete "MM" and insert --MRI--

Column 12, Line 55: delete "MM" and insert --MRI--

Column 12, Line 56: delete "MM" and insert --MRI--

Column 16, Line 31: delete "MM" and insert --MRI--

Signed and Sealed this
Twelfth Day of September, 2023

Katherine Kelly Vidal
*Director of the United States Patent and Trademark Office*